(12) United States Patent
Ansmann et al.

(10) Patent No.: US 8,329,147 B2
(45) Date of Patent: Dec. 11, 2012

(54) ALKYL BENZOATE MIXTURES

(75) Inventors: Achim Ansmann, Erkrath (DE); Rolf Kawa, Monheim (DE); Hans-Dieter Clages, Hilden (DE); Lars Zander, Rommerskirchen (DE)

(73) Assignee: Cognis IP Management GmbH, Duesseldorf (DE)

( * ) Notice: Subject to any disclaimer, the term of this patent is extended or adjusted under 35 U.S.C. 154(b) by 604 days.

(21) Appl. No.: 12/443,336

(22) PCT Filed: Sep. 18, 2007

(86) PCT No.: PCT/EP2007/008103
§ 371 (c)(1),
(2), (4) Date: Mar. 27, 2009

(87) PCT Pub. No.: WO2008/037380
PCT Pub. Date: Apr. 3, 2008

(65) Prior Publication Data
US 2010/0028275 A1  Feb. 4, 2010

(30) Foreign Application Priority Data
Sep. 27, 2006 (EP) .................................... 06020202

(51) Int. Cl.
*A61K 8/37* (2006.01)
*A61K 31/235* (2006.01)
*A61Q 17/04* (2006.01)

(52) U.S. Cl. .......... 424/59; 514/532; 514/785; 514/844; 514/969

(58) Field of Classification Search ........................ None
See application file for complete search history.

(56) References Cited

U.S. PATENT DOCUMENTS

| 2,428,450 | A |   | 10/1947 | Eitelman et al. |        |
|-----------|---|---|---------|-----------------|--------|
| 3,506,704 | A |   | 4/1970  | Miller et al.   |        |
| 4,275,222 | A | * | 6/1981  | Scala, Jr.      | 560/103 |
| 4,323,694 | A | * | 4/1982  | Scala, Jr.      | 424/59 |
| 5,028,417 | A | * | 7/1991  | Bhat et al.     | 424/59 |
| 5,783,173 | A | * | 7/1998  | Bonda et al.    | 424/59 |

FOREIGN PATENT DOCUMENTS

| DE | 197 12 033    | 9/1998  |
| EP | 0 693 471     | 1/1998  |
| EP | 0 694 521     | 1/1998  |
| EP | 0 818 450     | 1/1998  |
| WO | WO 2004/099117 | 11/2004 |

OTHER PUBLICATIONS

Finkel, P., "Formulierung Kosmetischer Sonnenschutzmittel," *Parfümerie und Kosmetick*, 80 Jahrgang, Nr 3, pp. 10-16 (1999).
Finkel, P., "Formulierung Kosmetischer Sonnenschutzmittel," *SOFW-Journal* 122 Jahrgang, Nr 8, pp. 543-548 (1996).
Anhang VII der europaischen Kosmetik-Gesetzgebung, 24th Commission Directive, Feb. 29, 2000. http://webinsight.airelresearch.com/arielft/eudoc/reg/t04836.htm last accessed on Feb. 25, 2011.

* cited by examiner

*Primary Examiner* — Ernst Arnold
*Assistant Examiner* — Christopher R Lea
(74) *Attorney, Agent, or Firm* — Diehl Servilla LLC

(57) ABSTRACT

The invention relates to alkyl benzoate mixtures, the sum of the C12- and C14-alkyl benzoates being greater than or equal to 85%, in relation to the total sum of the alkyl benzoates. The invention also relates to the use of said alkyl benzoate mixtures in cosmetic and/or pharmaceutical preparations, in particular as oil components.

11 Claims, No Drawings

ALKYL BENZOATE MIXTURES

CROSS REFERENCE TO RELATED APPLICATIONS

This application is the National Stage entry of PCT/EP2007/008103, filed Sep. 18, 2007, which claims priority to European patent application number EP 06020202.5 filed Sep. 27, 2006, both of which are incorporated herein by reference in their entireties.

FIELD OF THE INVENTION

The invention is in the field of cosmetic ingredients and relates to alkyl benzoate mixtures of defined composition.

BACKGROUND OF THE INVENTION

In the field of cosmetic preparations for skincare and hair care, a large number of requirements are imposed by the consumer: apart from cleaning and care effects, emphasis is placed on such differing parameters as the greatest possible dermatological compatibility, good refatting properties, elegant appearance, optimum sensory impression and storage stability.

Preparations which are used for the cleansing and care of human skin and hair generally comprise in particular oil bodies and water besides a series of surface-active substances. The oil bodies/emollients used are, for example, hydrocarbons, ester oils, and vegetable and animals oils/fats/waxes. In order to meet the high requirements in the marketplace with regard to sensory properties and optimum dermatological compatibility, new oil bodies are being continually developed and tested.

Particularly in preparations which comprise UV photoprotective filters, the solubility and stability of the UV photoprotective filters in the cosmetic preparations and in particular in the oil bodies is decisive for the UV photoprotective effect of the cosmetic product. At the same time, such oil bodies should both themselves and also primarily in the cosmetic preparations impart a sensorily light impression to these.

Various alkyl benzoates are known in the art as oil bodies for cosmetic preparations, thus, for example, the C12-C15 alkyl benzoates available under the trade names Cetiol®AB (Cognis Deutschland GmbH & Co. KG) or Finsolv®TN (Finetex) or the C16-C17 alkyl benzoates available under the trade name Finsolv® G-2 (Finetex), as well as the C18 alkyl benzoates available under the trade name Finsolv® 116 (Finetex).

However, the alkyl benzoates of the art are in need of improvement with regard to the solubility of UV photoprotective filters, in particular of crystalline UV photoprotective filters and also with regard to their sensory properties.

The object of the present invention was to provide oil bodies which are characterized in particular by an improved solubility for UV photoprotective filters and, compared with the known oil bodies, simultaneously have improved sensory properties.

Surprisingly, it has been found that alkyl benzoate mixtures with a defined alkyl chain distribution achieve the object according to the invention.

DETAILED DESCRIPTION OF PREFERRED EMBODIMENTS

Alkyl Benzoate Mixtures

The term "alkyl benzoate" encompasses esters of benzoic acid of the general formula (I), where R is an aliphatic, aromatic, saturated, mono- or polyunsaturated, linear and branched alkyl radicals having C4 to C22 carbon atoms.

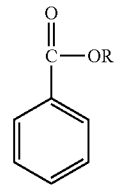

In a preferred embodiment, R is an aliphatic alkyl radical.

Accordingly, the term "C12-alkyl benzoate" describes a compound according to formula (I) in which R is a linear or branched, saturated or unsaturated alkyl radical having 12 carbon atoms. The term "alkyl benzoate with a carbon chain length of 12" is used synonymously for such compounds. Both terms encompass both individual compounds, such as, for example, dodecyl benzoate, and also a mixture of different alkyl benzoates in which C=12, such as, for example, dodecyl benzoate and 2-ethyl-1-decyl benzoate.

The invention relates to alkyl benzoate mixtures, characterized in that the fraction of uneven-numbered alkyl benzoates is less than or equal to 40%, in particular less than or equal to 30%, based on the total sum of the alkyl benzoates. In a preferred embodiment, the fraction of uneven-numbered alkyl benzoates is less than or equal to 20, in particular less than or equal to 10, less than or equal to 5, less than or equal to 3%, based on the total sum of the alkyl benzoates.

The % data of the alkyl benzoate mixtures are always % by weight of alkyl benzoate based on the total sum of the alkyl benzoates.

The term "alkyl benzoate mixture" refers to mixtures of alkyl benzoates with different carbon chain lengths. One embodiment thus encompasses mixtures which comprise at least 2 alkyl benzoates of differing alkyl chain length which are selected from the group of $C_8$ to $C_{16}$ alkyl benzoates. One preferred embodiment thus encompasses mixtures which comprise C12 and/or C14 alkyl benzoates.

"Uneven-numbered alkyl benzoates" is the term used to refer to the compounds of the formula (I) in which R is alkyl radical having 5, 7, 9, 11, 13, 15, 17, 19 and/or 21 carbon atoms.

One embodiment of the invention relates to alkyl benzoate mixtures, characterized in that the fraction of uneven-numbered alkyl benzoates is less than or equal to 50%, in particular less than or equal to 40%, in particular less than or equal to 10, less than or equal to 5, less than or equal to 3%, based on the total sum of the alkyl benzoates, and where the sum of the alkyl benzoates with a carbon chain length of less than or equal to 10 is less than or equal to 3%, based on the total sum of the alkyl benzoates. Preferably, the sum of the alkyl benzoates with a carbon chain length of less than or equal to 10 is less than or equal to 2%, in particular less than or equal to 1.5%, in particular less than or equal to 1%, based on the total sum of the alkyl benzoates.

One embodiment of the invention relates to alkyl benzoate mixtures, characterized in that the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates, and where the sum of the alkyl benzoates with a carbon chain length of greater than 14 is less than or equal to 15%, based on the total sum of the alkyl benzoates. Preferably, the sum of the alkyl benzoates with a carbon chain length of greater than 14 is less than or equal to 10%, preferably less than or equal to 8%, in particular less than or equal to 4%, in particular less than or equal to 2%, based on the total sum of the alkyl benzoates.

One embodiment of the invention relates to alkyl benzoate mixtures, characterized in that the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates, and where the sum of the alkyl benzoates with a carbon chain length of greater than 14 is less than or equal to 15%, preferably less than or equal to 10%, preferably less than or equal to 8%, in particular less than or equal to 4%, in particular less than or equal to 2%, based on the total sum of the alkyl benzoates, and the sum of the C12- and C14-alkyl benzoates is greater than or equal to 85%, preferably greater than or equal to 90%, in particular greater than or equal to 95%, based on the total sum of the alkyl benzoates.

One embodiment of the invention relates to alkyl benzoate mixtures, characterized in that the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates, and where the sum of the alkyl benzoates with a carbon chain length of greater than 14 is less than or equal to 15%, preferably less than or equal to 10%, preferably less than or equal to 8%, in particular less than or equal to 4%, in particular less than or equal to 2%, based on the total sum of the alkyl benzoates, and the sum of the alkyl benzoates with a carbon chain length of less than or equal to 10 is less than or equal to 3%, preferably less than or equal to 2%, in particular less than or equal to 1.5%, in particular less than or equal to 1%, based on the total sum of the alkyl benzoates.

One embodiment of the invention relates to alkyl benzoate mixtures, characterized in that the fraction of uneven-numbered alkyl benzoates is less than or equal to 50%, in particular less than or equal to 40%, preferably less than or equal to 30%, in particular less than or equal to 10, less than or equal to 5, less than or equal to 3%, based on the total sum of the alkyl benzoates, and where the sum of the alkyl benzoates with a carbon chain length of greater than 14 is less than or equal to 15%, preferably less than or equal to 10%, preferably less than or equal to 8%, in particular less than or equal to 4%, in particular less than or equal to 2%, based on the total sum of the alkyl benzoates, and the sum of the C12- and C14-alkyl benzoates is greater than or equal to 85%, preferably greater than or equal to 90%, in particular greater than or equal to 95%, based on the total sum of the alkyl benzoates, and the sum of the alkyl benzoates with a carbon chain length of less than or equal to 10 is less than or equal to 3%, preferably less than or equal to 2%, in particular less than or equal to 1.5%, in particular less than or equal to 1%, based on the total sum of the alkyl benzoates.

The invention further relates to alkyl benzoate mixtures where the sum of the C12- and C14-alkyl benzoates is greater than or equal to 85%, based on the total sum of the alkyl benzoates. Preferably, the sum of the C12- and C14-alkyl benzoates is greater than or equal to 90%, in particular greater than or equal to 95%, based on the total sum of the alkyl benzoates.

The remaining fraction of the alkyl benzoates usually consists of compounds of the formula (I) in which R is a C number between C4 and C22, in particular between C6 and C20.

Particular preference is given to alkyl benzoate mixtures where the sum of the C12- and C14-alkyl benzoates is greater than or equal to 85%, based on the total sum of the alkyl benzoates, and where the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates.

Preferably, the sum of the C12- and C14-alkyl benzoates is greater than or equal to 90%, in particular greater than or equal to 95%, based on the total sum of the alkyl benzoates, and the fraction of branched alkyl benzoates is less than or equal to 50%, in particular less than or equal to 40%, preferably less than or equal to 30%.

The present invention further provides an alkyl benzoate mixture, where the sum of the C12- and C14-alkyl benzoates is greater than or equal to 85%, based on the total sum of the alkyl benzoates, and where the sum of the alkyl benzoates with a carbon chain length of less than or equal to 10 is less than or equal to 3%, based on the total sum of the alkyl benzoates. Preferably, the sum of the alkyl benzoates with a carbon chain length of less than or equal to 10 is less than or equal to 2%, in particular less than or equal to 1.5%, in particular less than or equal to 1%, based on the total sum of the alkyl benzoates.

The present invention further provides an alkyl benzoate mixture, where the sum of the C12- and C14-alkyl benzoates is greater than or equal to 85%, based on the total sum of the alkyl benzoates, and where the sum of the alkyl benzoates with a carbon chain length of less than or equal to 10 is less than or equal to 3%, based on the total sum of the alkyl benzoates. Preferably, the sum of the alkyl benzoates with a carbon chain length of less than or equal to 10 is less than or equal to 2%, in particular less than or equal to 1.5%, in particular less than or equal to 1%, based on the total sum of the alkyl benzoates, and where the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates.

The present invention further provides alkyl benzoate mixtures comprising C12 and/or C14 alkyl benzoates, where the sum of the alkyl benzoates with a carbon chain length of greater than 14 is less than or equal to 15%, based on the total sum of the alkyl benzoates. Preferably, the sum of the alkyl benzoates with a carbon chain length of greater than 14 is less than or equal to 10%, preferably less than or equal to 8%, in particular less than or equal to 4%, in particular less than or equal to 2%, based on the total sum of the alkyl benzoates.

Preference is given to alkyl benzoate mixtures comprising C12 and/or C14 alkyl benzoates, where the sum of the alkyl benzoates with a carbon chain length of greater than 14 is less than or equal to 15, preferably less than or equal to 10%, preferably less than or equal to 8%, in particular less than or equal to 4%, in particular less than or equal to 2%, based on the total sum of the alkyl benzoates, and where the sum of the alkyl benzoates with a carbon chain length of less than or equal to 10 is less than or equal to 3%, preferably less than or equal to 2%, in particular less than or equal to 1.5%, in particular less than or equal to 1%, based on the total sum of the alkyl benzoates.

A preferred embodiment of the invention relates to alkyl benzoate mixtures where the sum of the C12- and C14-alkyl benzoates is greater than or equal to 85%, based on the alkyl benzoates, and the sum of the alkyl benzoates with a carbon chain length of greater than 14 is less than or equal to 15%, based on the total sum of the alkyl benzoates.

A preferred embodiment of the invention relates to alkyl benzoate mixtures where the sum of the C12- and C14-alkyl benzoates is greater than or equal to 85%, based on the total sum of the alkyl benzoates, and the sum of the alkyl benzoates with a carbon chain length of less than or equal to 10 is less than or equal to 15% and the sum of the alkyl benzoates with a carbon chain length of greater than 14 is less than or equal to 15%, based on the total sum of the alkyl benzoates.

In all of these embodiments, the sum of the C12- and C14-alkyl benzoates is in each case preferably greater than or equal to 90%, in particular greater than or equal to 95%, based on the total sum of the alkyl benzoates.

In all of these embodiments, the sum of the alkyl benzoates with a carbon chain length of less than or equal to 10 is in each case preferably less than or equal to 2%, in particular less than or equal to 1.5%, in particular less than or equal to 1%, based on the total sum of the alkyl benzoates.

In all of these embodiments, the sum of the alkyl benzoates with a carbon chain length of greater than 14 is in each case preferably less than or equal to 10%, preferably less than or equal to 8%, in particular less than or equal to 4%, in particular less than or equal to 2%, based on the total sum of the alkyl benzoates.

The invention further provides alkyl benzoate mixtures where the alkyl benzoates have the following carbon chain distribution:
(a) C12 alkyl benzoates greater than or equal to 60% and
(b) C14 alkyl benzoates between 15% and 40%, based on the total sum of the alkyl benzoates.

In a particularly preferred embodiment of this invention, the sum of the C12-alkyl benzoates is greater than or equal to 65%, in particular greater than or equal to 70%, based on the total sum of the alkyl benzoates.

In a particularly preferred embodiment of this invention, the sum of the C14-alkyl benzoates is between 20% and 35%, preferably between 25% and 30%, based on the total sum of the alkyl benzoates.

The invention further provides alkyl benzoate mixtures where the alkyl benzoates have the following carbon chain distribution:
(a) C12 alkyl benzoates greater than or equal to 60% and
(b) C14 alkyl benzoates between 15% and 40%, based on the total sum of the alkyl benzoates, and the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates.

A preferred embodiment of the invention relates to alkyl benzoate mixtures where the alkyl benzoates have the following carbon chain distribution:
(a) C12 alkyl benzoates greater than or equal to 60% and (b) C-14 alkyl benzoates between 15% and 40% and the sum of the alkyl benzoates with a carbon chain length of less than or equal to 10 is less than or equal to 3%, in particular less than or equal to 2%, preferably less than or equal to 1%, in each case based on the total sum of the alkyl benzoates. In a particularly preferred embodiment of this invention, the sum of the C12-alkyl benzoates is greater than or equal to 65%, in particular greater than or equal to 70%, based on the total sum of the alkyl benzoates. In a particularly preferred embodiment of this invention, the sum of the C14-alkyl benzoates is between 20% and 35%, preferably between 25% and 30%, based on the total sum of the alkyl benzoates.

A preferred embodiment of the invention relates to alkyl benzoate mixtures where the alkyl benzoates have the following carbon chain distribution:
(a) C12 alkyl benzoates greater than or equal to 60% and (b) C-14 alkyl benzoates between 15% and 40% and the sum of the alkyl benzoates with a carbon chain length of less than or equal to 10 is less than or equal to 3%, in particular less than or equal to 2%, preferably less than or equal to 1%, in each case based on the total sum of the alkyl benzoates, and the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates. In a particularly preferred embodiment of this invention, the sum of the C12-alkyl benzoates is greater than or equal to 65%, in particular greater than or equal to 70%, based on the total sum of the alkyl benzoates. In a particularly preferred embodiment of this invention, the sum of the C14-alkyl benzoates is between 20% and 35%, preferably between 25% and 30%, based on the total sum of the alkyl benzoates.

A preferred embodiment of the invention relates to alkyl benzoate mixtures where the alkyl benzoates have the following carbon chain distribution:
(a) C12-alkyl benzoates greater than or equal to 60% and (b) C-14-alkyl benzoates between 15% and 40% and the sum of the alkyl benzoates with a carbon chain length of greater than 14 is less than or equal to 15%, in particular less than or equal to 10%, preferably less than or equal to 8%, in particular less than or equal to 4%, in particular less than or equal to 2%, in each case based on the total sum of the alkyl benzoates. In a particularly preferred embodiment of this invention, the sum of the C12-alkyl benzoates is greater than or equal to 65%, in particular greater than or equal to 70%, based on the total sum of the alkyl benzoates. In a particularly preferred embodiment of this invention, the sum of the C14-alkyl benzoates is between 20% and 35%, preferably between 25% and 30%, based on the total sum of the alkyl benzoates.

A preferred embodiment of the invention relates to alkyl benzoate mixtures, where the alkyl benzoates have the following carbon chain distribution:
(a) C12-alkyl benzoates greater than or equal to 60% and (b) C-14-alkyl benzoates between 15% and 40% and the sum of the alkyl benzoates with a carbon chain length of greater than 14 is less than or equal to 15%, in particular less than or equal to 10%, preferably less than or equal to 8%, in particular less than or equal to 4%, in particular less than or equal to 2%, in each case based on the total sum of the alkyl benzoates, and the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates. In a particularly preferred embodiment of this invention, the sum of the C12-alkyl benzoates is greater than or equal to 65%, in particular greater than or equal to 70%, based on the total sum of the alkyl benzoates. In a particularly preferred embodiment of this invention, the sum of the C14-alkyl benzoates is between 20% and 35%, preferably between 25% and 30%, based on the total sum of the alkyl benzoates.

A particularly preferred embodiment of the invention relates to alkyl benzoate mixtures where the alkyl benzoates have the following carbon chain distribution: (a) C12-alkyl benzoates greater than or equal to 60% and (b) C-14-alkyl benzoates between 15% and 40% and the sum of the alkyl benzoates with a carbon chain length of less than or equal to 10 is less than or equal to 3%, in particular less than or equal to 2%, preferably less than or equal to 1%, and the sum of the alkyl benzoates with a carbon chain length of greater than 14 is less than or equal to 15%, in particular less than or equal to 10%, preferably less than or equal to 8%, in particular less than or equal to 4%, preferably less than or equal to 2%, in each case based on the total sum of the alkyl benzoates. In a particularly preferred embodiment of this invention, the sum of the C12-alkyl benzoates is greater than or equal to 65%, in particular greater than or equal to 70%, based on the total sum of the alkyl benzoates. In a particularly preferred embodiment of this invention, the sum of the C14-alkyl benzoates is between 20% and 35%, preferably between 25% and 30%, based on the total sum of the alkyl benzoates.

A particularly preferred embodiment of the invention relates to alkyl benzoate mixtures where the alkyl benzoates have the following carbon chain distribution: (a) C12-alkyl benzoates greater than or equal to 60% and (b) C-14-alkyl benzoates between 15% and 40% and the sum of the alkyl benzoates with a carbon chain length of less than or equal to 10 is less than or equal to 3%, in particular less than or equal to 2%, preferably less than or equal to 1%, and the sum of the alkyl benzoates with a carbon chain length of greater than 14 is less than or equal to 15%, in particular less than or equal to 10%, preferably less than or equal to 8%, in particular less than or equal to 4%, preferably less than or equal to 2%, in each case based on the total sum of the alkyl benzoates and the fraction of uneven-numbered alkyl benzoates is less than or equal to 50%, in particular less than or equal to 40%, preferably less than or equal to 30, in particular less than or equal to 10, less than or equal to 5, less than or equal to 3%, based on the total sum of the alkyl benzoates. In a particularly preferred embodiment of this invention, the sum of the C12-alkyl benzoates is greater than or equal to 65%, in particular greater than or equal to 70%, based on the total sum of the alkyl benzoates. In a particularly preferred embodiment of this invention, the sum of the C14-alkyl benzoates is between 20% and 35%, preferably between 25% and 30%, based on the total sum of the alkyl benzoates.

A further embodiment of the present invention relates to any hitherto specified alkyl benzoate mixture where the sum of the branched alkyl benzoates is less than or equal to 10%, preferably less than or equal to 5%, based on the total sum of the alkyl benzoates.

None of the known alkyl benzoate mixtures in the art has the distributions according to the invention. Surprisingly, it has been found that mixtures with the carbon chain distribution according to the invention are not only highly spreading oil bodies, but at the same time have an improved dissolving power for UV photoprotective filters compared with the known alkyl benzoates.

Preparation

The alkyl benzoates are prepared by processes known to the person skilled in the art. The alkyl benzoates can, for example, be obtained by reacting benzoic acid with the corresponding alcohol or alcohol mixture in the presence of a catalyst. One such process is described, for example, in WO 2004/099117.

The alkyl benzoates can likewise be obtained by reacting methyl esters of benzoic acid with an alcohol mixture, the alcohol mixture having the carbon distribution according to the invention which is then to be found again in the alkyl benzoate mixture.

The alkyl benzoate mixtures according to the invention can be obtained by using alcohol mixtures which has the carbon distribution according to the invention in the reaction. The alkyl benzoate mixtures according to the invention can likewise be obtained by mixing the corresponding individual alkyl benzoates.

The odor of the products obtained by esterification or transesterification can be improved if necessary through deodorization; the color can likewise be improved if desired through treatment with methods known to the person skilled in the art.

Customary alcohol mixtures which are suitable for the preparation of the alkyl benzoate mixtures according to the invention have, for example, the following carbon chain distribution: sum of the C6 to C10 fatty alcohols is less than or equal to 3%, the sum of the C12 fatty alcohols is 60 to 80%, C14 fatty alcohols 15 to 40%, C16 less than or equal to 4%, sum of the fatty alcohols with a carbon chain greater than 16 is less than or equal to 0.5%. Fatty alcohol mixtures which are suitable for preparing the alkyl benzoates according to the invention are obtainable, for example, under the trade name Lorol® Spezial (Synative AL S) from Cognis.

Suitable fatty alcohol mixtures usually have the following fatty alcohol distribution: fatty alcohols with the carbon chain of 12>65%, in particular >70%. Fatty alcohols with a carbon chain of 14>20%, in particular greater than 22%. The content of fatty alcohols with a carbon chain of greater than 16 is generally below 8%, in particular below 4%.

Fatty alcohol mixtures of the following composition are particularly suitable:
C12 70-75%; C14 24-30%, C16 below 4% or
C12 65-71%, C14 22-28%, C16 below 8%.

Both aliphatic, aromatic, saturated, mono- and polyunsaturated, linear and branched alkyl radicals are encompassed. In a preferred embodiment of the invention, primarily (i.e. more than 50%, preferably more than 60%, in particular more than 70%, particularly preferably above 90%, of the particular alkyl radical) aliphatic, linear alcohols of the stated carbon number are used, such as, for example, 1-dodecanol (lauryl alcohol) as C12 fatty alcohol and tetradecanol (myristyl alcohol) as C14 fatty alcohol.

Cosmetic and/or Pharmaceutical Preparations

The alkyl benzoate mixtures according to the invention permit the preparation of stable cosmetic and pharmaceutical emulsions.

The present invention therefore further provides the use of the alkyl benzoate mixtures according to the invention in cosmetic and/or pharmaceutical preparations, in particular as oil bodies. The alkyl benzoate mixtures according to the invention can be used in this connection, depending on the preparation, either as the sole oil body or else in combination with further oil bodies.

The alkyl benzoate mixtures according to the invention are particularly suitable for the dissolution and/or stabilization of UV photoprotective filters. The invention therefore provides cosmetic and/or pharmaceutical preparations comprising at least one alkyl benzoate mixture according to at least one of claims 1 to 9 and also at least one UV photoprotective filter.

According to the invention, suitable UV photoprotective filters are organic substances (photoprotective filters) which are crystalline or liquid at room temperature and which are able to absorb ultraviolet rays and release the absorbed energy again in the form of longer-wave radiation, e.g. heat. UV filters may be oil-soluble or water-soluble. Examples of typical oil-soluble UV-B filters and/or broad spectrum UV A/B filters are:

3-benzylidenecamphor or 3-benzylidenenorcamphor (Mexoryl SDS 20) and derivatives thereof, e.g. 3-(4-methylbenzylidene)camphor, as described in EP 0693471 B1;

3-(4'-trimethylammonium)benzylidenebornan-2-one methyl sulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL)

polymer of N-{(2 and 4)-[2-oxoborn-3-ylidene) methyl}benzyl]acrylamide (Mexoryl SW)

2-(2H-benzotriazol-2-yl)-4-methyl-6-(2-methyl-3-(1,3,3,3-tetramethyl-1-(trimethylsilyloxy)disiloxanyl)propyl)phenol (Mexoryl XL)

4-aminobenzoic acid derivatives, preferably 2-ethylhexyl 4-(dimethylamino)benzoate, 2-octyl 4-(dimethylamino) benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomethyl salicylate;

derivatives of benzophenone, preferably 2-hydroxy-4-methoxybenzophenone, 2-hydroxy-4-methoxy-4'-methyl-benzophenone, 2,2'-dihydroxy-4-methoxybenzophenone;

esters of benzalmalonic acid, preferably di-2-ethylhexyl 4-methoxybenzmalonate;

triazine derivatives, such as, for example, 2,4,6-trianilino(p-carbo-2'-ethyl-1'-hexyloxy)-1,3,5-triazine and 2,4,6-tris[p-(2-ethylhexyloxycarbonyl)anilino]-1,3,5-triazine (Uvinul T 150), as described in EP 0818450 A1 or bis(2-ethylhexyl) 4,4'-[(6-[4-((1,1-dimethylethyl)aminocarbonyl)phenylamino]-1,3,5-triazine-2,4-diyl)diimino]bisbenzoate (Uvasorb® HEB);

2,2-(methylenebis(6-(2H-benzotriazol-2-yl)-4-(1,1,3,3-tetramethylbutyl)phenol) (Tinosorb M);

2,4-bis[4-(2-ethylhexyloxy)-2-hydroxyphenyl]-6-(4-methoxyphenyl)-1,3,5-triazine (Tinosorb S);

propane-1,3-diones, such as, for example, 1-(4-tert-butylphenyl)-3-(4'-methoxyphenyl)propane-1,3-dione;

ketotricyclo(5.2.1.0)decane derivatives, as described in EP 0694521 B1;

dimethicodiethylbenzalmalonates (Parsol SLX).

Suitable water-soluble UV filters are:

2-phenylbenzimidazole-5-sulfonic acid and the alkali metal, alkaline earth metal, ammonium, alkylammonium, alkanolammonium and glucammonium salts thereof;

2,2(-(1,4-phenylene)bis(1H-benzimidazole-4,6-disulfonic acid, monosodium salt) (Neo Heliopan AP)

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidene-methyl)benzenesulfonic acid and 2-methyl-5-(2-oxo-3-bornylidene)sulfonic acid and salts thereof.

Suitable typical UV-A filters are in particular derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds, as described in DE 19712033 A1 (BASF), and benzoic acid, 2-[4-(diethylamino)-2-hydroxybenzoyl], hexyl ester (Uvinul® A plus).

The UV-A and UV-B filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Such combinations are advantageously combined with water-soluble filters, such as, for example, 2-phenylbenzimidazole-5-sulfonic acid and the alkali metal, alkaline earth metal, ammonium, alkylammonium, alkanolammonium and glucammonium salts thereof. According to the invention, UV photoprotective filters are preferably selected from Annex VII of the European Cosmetics Legislation (24th Adapting Commission Directive, Feb. 29, 2000).

Besides the specified soluble substances, insoluble photoprotective pigments, namely finely disperse metal oxides and/or salts, are also suitable. Examples of suitable metal oxides are in particular zinc oxide and titanium dioxide and in addition oxides of iron, zirconium, silicon, manganese, aluminum and cerium, and mixtures thereof. Salts which can be used are silicates (talc), barium sulfate or zinc stearate. The oxides and salts are used in the form of the pigments for skincare and skin-protecting emulsions and also for decorative cosmetics. The particles should have an average diameter of less than 100 nm, preferably between 5 and 50 nm and in particular between 15 and 30 nm. They can have a spherical form, although it is also possible to use those particles which have an ellipsoidal form or a form which deviates in some other way from the spherical shape. The pigments may also be present in surface-treated, i.e. hydrophilized or hydrophobized, form. Typical examples are coated titanium dioxides, such as, for example, titanium dioxide T 805 (Degussa) or Eusolex® T, Eusolex® T-2000, Eusolex® T-Aqua, Eusolex® AVO, Eusolex® T-ECO, Eusolex® T-OLEO and Eusolex® T-S (Merck). Typical examples are zinc oxides, such as, for example, zinc oxide neutral, zinc oxide NDM (Symrise) or Z-Cote® (BASF) or SUNZ-nO-AS and SUNZnO-NAS (Sunjun Chemical Co. Ltd.). Suitable hydrophobic coating compositions in this connection are primarily silicones and of these specifically trialkoxyoctylsilanes or simethicones. In sunscreen compositions, preference is given to using so-called micropigments or nanopigments. Preferably, micronized zinc oxide is used. Further suitable UV photoprotective filters can be found in the review by P. Finkel in SÖFW-Journal 122, 543 (1996) and Parf. Kosm. 3, 11 (1999).

Besides the two aforementioned groups of primary photoprotective substances, it is also possible to use secondary photoprotective agents of the antioxidant type which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, lipoic acid and derivatives therefore (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, linoleyl, cholesteryl and glyceryl esters thereof), and also salts thereof, dilauryl thiodipropionate, distearyl thiodipropionate, thiodipropionic acid and derivatives (esters, ethers, peptides, lipids, nucleotides, nucleosides and salts) thereof, and also sulfoximine compounds (e.g. buthionine sulfoximines, homocysteine sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate), and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

A preferred embodiment of the invention relates to cosmetic and/or pharmaceutical preparations comprising at least one alkyl benzoate mixture according to at least one of claims 1 to 9 and at least one UV photoprotective filter selected from the group consisting of 4-methylbenzylidenecamphor, benzophenone-3, butylmethoxydibenzoylmethane, bis-ethylhexyl-oxyphenol methoxyphenyltriazine, methylene bisbenzotriazolyl tetramethylbutylphenol, diethylhexylbutamidotriazone, ethylhexyltriazone and diethylaminohydroxybenzoyl hexyl benzoate.

These UV photoprotective filters are commercially available, for example, under the following trade names: Neo Heliopan MBC (INCI: 4-methylbenzylidene camphor; manufacturer: Symrise); Neo Heliopan BB (INCI: benzophenone-3, manufacturer: Symrise); Parsol 1789 (INCI: butylmethoxydibenzoylmethane, manufacturer: Hoffmann-La Roche (Givaudan)); Tinosorb S (INCI: bis-ethylhexyloxyphenol methoxyphenol triazine; manufacturer: Ciba Specialty Chemicals Corporation); Tinosorb M (INCI: methylene bis-benzotriazolyl tetramethylbutylphenol, manufacturer: Ciba Specialty Chemicals Corporation), Uvasorb HEB (INCI: diethylhexyl butamido triazone, manufacturer: 3V Inc.), Uvinul T 150 (INCI: ethylhexyl triazone, manufacturer: BASF AG), Uvinul A plus (INCI: diethylamino hydroxybenzoyl hexyl benzoate, manufacturer: BASF AG).

The alkyl benzoate mixtures according to the invention can be used in cosmetic and/or pharmaceutical preparations in concentrations of from 1 to 90%. The preferred use range is between 1 and 50%, in particular 2% and 20%, based on the total weight of the cosmetic and/or pharmaceutical preparation. Fields of use are, for example, cosmetic and/or pharmaceutical O/W or W/O care emulsions, sunscreen formulation, antiperspirant/deodorant concepts, formulations for decorative cosmetics, oily care preparations, impregnation liquids for substrates, such as, for example, paper and fleece products. By way of example, mention may be made of wet wipes, tissues, diapers or hygiene products.

The alkyl benzoate mixtures according to the invention are suitable in particular for a sprayable application and/or are suitable as care emulsion for tissues, papers, wipes, sponges (e.g. polyurethane sponges), plasters in the sector of baby hygiene, baby care, skincare, sun protection, aftersun treatment, insect repellant, cleaning, facial cleansing and antiperspirant/deodorant application. Through the use of the alkyl benzoate mixtures according to the invention, the sensory behavior upon application is positively influenced.

The cosmetic and/or pharmaceutical preparations may be formulations for body care, e.g. a body milk, creams, lotions, sprayable emulsions, products for eliminating body odor etc. The alkyl benzoate mixtures can also be used in surfactant-containing formulations, such as, for example, foam baths and shower baths, hair shampoos and care rinses. Depending on the intended application, the cosmetic formulations comprise a series of further auxiliaries and additives, such as, for example, surfactants, further oil bodies, emulsifiers, pearlescent waxes, consistency regulators, thickeners, superfatting agents, stabilizers, polymers, fats, waxes, lecithins, phospholipids, biogenic active ingredients, deodorants, antiperspirants, antidandruff agents, film formers, swelling agents, insect repellants, self-tanning agents, tyrosinase inhibitors (depigmentation agents), hydrotropes, solubilizers, preservatives, perfume oils, dyes etc., which are listed below by way of example.

Surface-active substances which may be present are anionic, nonionic, cationic and/or amphoteric or zwitterionic surfactants. Preferably at least one anionic surfactant is present in surfactant-containing cosmetic preparations, such as, for example, shower gels, foam baths, shampoos etc. The fraction of the surfactants here is usually about 1 to 30% by weight, preferably 5 to 25% by weight and in particular 10 to 20% by weight.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxyl mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular vegetable products based on wheat) and alkyl (ether) phosphates. If the anionic surfactants contain polyglycol ether chains, these can have a conventional, but preferably a narrowed, homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolyzates (in particular vegetable products based on wheat), polyol fatty acid esters, sugar esters, sorbitan esters, polysorbates and amine oxides. If the nonionic surfactants contain polyglycol ether chains, these can have a conventional, but preferably a narrowed, homolog distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric and zwitterionic surfactants are alkylbetaines, alkylaminobetaines, aminopropionates, aminoglycinates, imidazolinium betaines and sulfobetaines. The specified surfactants are exclusively known compounds. With regard to structure and preparation of these substances, reference may be made to relevant review papers in this field. Typical examples of particularly suitable mild, i.e. particularly skin-compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably being based on wheat proteins.

Body care compositions, such as creams, lotions and milks, usually comprise a series of further oil bodies and emollients which contribute to further optimizing the sensory properties. Depending on the type of formulation, the oil bodies can be present in a total amount of from 1 to 90% by weight, in particular in a total amount of 1-50% by weight, preferably 5-25% by weight and in particular 5-15% by weight. Further oil bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkylhydrocyarboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol) and/or Guerbert alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN) which differ from the alkyl benzoates according to the invention, linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols.

Fats and waxes are added to the body care products as care substances and also in order to increase the consistency of the cosmetics. Typical examples of fats are glycerides, i.e. solid vegetable or animal products which consist essentially of mixed glycerol esters of higher fatty acids. Fatty acid partial glycerides, i.e. technical-grade mono- and/or diesters of glycerol with fatty acids having 12 to 18 carbon atoms, such as, for example, glycerol mono/dilaurate, -palmitate or -stearate, are also suitable here. Suitable waxes are, inter alia, natural waxes, such as, for example, candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial grease, ceresine, ozokerite (earth wax), petrolatum, paraffin waxes, microwaxes; chemically modified waxes (hard waxes), such as, for example, montan ester waxes, sasol waxes, hydrogenated jojoba waxes, and also synthetic waxes, such as, for example, polyalkylene waxes and polyethylene glycol waxes. Besides the fats, suitable additives are also fat-like substances, such as lecithins and phospholipids. Examples of natural lecithins which may be mentioned are the cephalins, which are also referred to as phosphatidic acids and are derivatives of 1,2-diacyl-sn-glycerol-3-phosphoric acids. By contrast, phospholipids are generally understood as meaning mono- and preferably diesters of phosphoric acid with glycerol (glycerol phosphates), which are generally included amongst the fats. In addition, sphingosines and sphingolipids are also suitable.

Suitable thickeners are, for example, Aerosil grades (hydrophilic silicas), polysaccharides, in particular xanthan gum, guar guar, agar agar, alginates and tyloses, carboxymethylcellulose and hydroxyethyl- and hydroxypropylcellulose, polyvinyl alcohol, polyvinylpyrrolidone and bentonites, such as, for example, Bentone® Gel VS-5PC (Rheox).

Biogenic active ingredients are to be understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prune extract, bambara nut extract and vitamin complexes.

Deodorizing active ingredients counteract, mask or eliminate body odors. Body odors are formed by the action of skin bacteria on apocrine perspiration, during which unpleasant-smelling degradation products are formed. Accordingly, suitable deodorizing active ingredients are, inter alia, antimicrobial agents, enzyme inhibitors, odor absorbers or odor maskers.

Suitable insect repellants are, for example, N,N-diethyl-m-toluamide, 1,2-pentanediol or ethyl 3-(N-n-butyl-N-acetylamino)propionate, which is sold under the name Insect Repellent® 3535 by Merck KGaA, and butylacetylaminopropionate.

A suitable self-tanning agent is dihydroxyacetone. Suitable tyrosine inhibitors, which prevent the formation of melanin and are used in depigmentation compositions, are, for example, arbutin, ferulic acid, kojic acid, coumaric acid and ascorbic acid (vitamin C).

Suitable preservatives are, for example, phenoxyethanol, formaldehyde solution, parabens, pentanediol or sorbic acid, and the silver complexes known under the name Surfacine® and the other substance classes listed in Annex 6, part A and B of the Cosmetics Ordinance.

Perfume oils which may be mentioned are mixtures of natural and synthetic fragrances. Natural fragrances are extracts from flowers, stems and leaves, fruits, fruit peels, woods, herbs and grasses, needles and branches, resins and balsams. Animal raw materials, such as, for example, civet and castoreum, and also synthetic fragrance compounds of the ester, ether, aldehyde, ketone, alcohol and hydrocarbon types, are also suitable.

Suitable pearlescent waxes, in particular for use in surface-active formulations, are, for example: alkylene glycol esters, specifically ethylene glycol stearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in sum at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Superfatting agents which may be used are substances such as, for example, lanolin and lecithin, and also polyethoxylated or acylated lanolin and lecithin derivatives, polyol fatty acid esters, monoglycerides and fatty acid alkanolamides, the latter also serving as foam stabilizers.

Stabilizers which can be used are metal salts of fatty acids, such as, for example, magnesium, aluminum and/or zinc stearate and/or ricinoleate.

To improve the flow behavior, hydrotropes, such as, for example, ethanol, isopropyl alcohol, or polyols, can also be used. Suitable polyols preferably have 2 to 15 carbon atoms and at least two hydroxyl groups. The polyols can also contain further functional groups, in particular amino groups, and/or be modified with nitrogen.

EXAMPLES

Example A According to the Invention

Preparation

The fatty alcohol mixture Lorol®Spezial (Cognis; fatty alcohol distribution C12 70-75%, C14 24-30%, C16 below 4%) and benzoic acid were esterified under Sn(II) catalysis at 180 to 230° C. with elimination of water at atmospheric pressure and later in a slight vacuum. The excess alcohol was then distilled off in vacuo and the reaction product was cooled. The catalyst was removed and the product was deodorized.

Comparative Example B

The commercially available product Finsolv®TN (Finetex) serves as comparative example. The table below shows the carbon chain distribution of example A according to the invention and also of comparative example B.

| Carbon chain distribution | Example A (according to the invention) | Example B (comparison) |
| --- | --- | --- |
| C12, linear | 70-75% | 22.7% |
| C12, branched | <1% | 3.1% |
| Total C12 | 70-75% | 25.8% |
| C13, linear | | 31.8% |
| C13, branched | | 4.5% |
| Total C13 | <1% | 36.3% |
| C14, linear | 24-30% | 17.5% |
| C14, branched | <1% | 3.7% |
| Total C14 | | 21.2% |
| C15, linear | | 14.5% |
| C15, branched | | 2.1% |
| Total C15 | <1% | 16.6% |
| ≧C16 | <4% | 0.1% |

Example 1

Sensory Evaluation

The sensory evaluation of example A according to the invention was made relative to comparative example B: a panel consisting of 12 experts carried out the sensory evaluation. The following criteria based on the end feel on the skin were assessed: softness, smoothness, care. At the same time, the acceptance was also assessed.

The evaluation of these criteria was made using grades from 1 (little) to 7 (much).

| Criteria | Example A according to the invention | Comparative example B Finsolv ® TN (Finetex) |
| --- | --- | --- |
| Smoothness | 7 | 5 |
| Softness | 6 | 4 |
| Care | 7 | 5 |
| Acceptance | 7 | 4 |

Compared with the art, example A according to the invention exhibits improved sensory properties coupled with a high acceptance.

Solubility of Various UV Photoprotective Filters

To determine the solubility, various commercially available UV photoprotective filters were dissolved in the alkyl benzoate mixture according to the invention (according to example A) or in the commercially available C12-C15 alkyl benzoates, Finsolv®TN at elevated temperature at 80° C., and stored for 1 week at 15° C. The table below shows the amount of UV filter in % by wt. which remains clear in solution following storage for 1 week at 15° C.

| | Solubility [% by wt.] |
| --- | --- |
| Alkyl benzoate mixture according to example 1 plus Uvinul ® T 150 | 10 |
| Finsolv ® TN plus Uvinul T 150 | 5 |
| Alkyl benzoate mixture according to example 1 plus Neoheliopan ® BB | 15 |
| Finsolv ® TN1 plus Neoheliopan BB | 10 |
| Alkyl benzoate mixture according to example 1 plus Parsol ® 1789 | 15 |
| Finsolv ® TN plus Parsol 1789 | 10 |

Uvinul® 150; INCI: Ethylhexyl Triazone (BASF AG) Neo Heliopan®BB; INCI: Benzophenone-3 (Symrise) Parsol®1789; INCI: Butyl Methoxydibenzoylmethane (DSM Nutritional Products)

Cosmetic Preparations: Formulations for Spray and Wipe Applications and also for Antiperspirant/Deodorant Concepts Formulations 1 to 26 describe stable formulations based on the oil component according to the invention, in particular of preparation example A, which are suitable particularly for an application as pump or aerosol spray and/or as care emulsion for tissues, papers, wipes, sponges (e.g. polyurethane sponges), plasters in the sector of baby hygiene, baby care, skincare, sun protection, aftersun treatment, insect repellant, cleansing, facial cleansing and antiperspirant/deodorant application. In the case of application as aerosol spray, propellant gases such as propane, butane, isobutane or mixtures are particularly suitable. The use of the oil component according to the invention positively influences the sensory behavior upon application. The quantitative data refer in each case to % by wt. of the standard commercial substances in the overall composition.

TABLE 1

Formulations 1 to 13

| Components INCI (trade name) | 1 | 2 | 3 | 4 | 5 | 6 | 7 | 8 | 9 | 10 | 11 | 12 | 13 |
|---|---|---|---|---|---|---|---|---|---|---|---|---|---|
| Emulgade ® SE | | | | | | | | | | | | 10.7 | 5.1 |
| Eumulgin ® B2 | | | | | | | | | | | | 5.8 | 3.4 |
| Emulgade ® PL 68/50 | 1 | | 1 | 1 | | 2 | 2 | | 2 | | 2 | | |
| Eumulgin ® VL 75 | | 1 | | | 1 | | | 3 | | 2.5 | | | |
| Lanette ® E | 1 | 1 | 1 | | 1 | | | | 1 | 1 | | | |
| Emulgade ® SUCRO | 1 | 1.5 | | | | | 1 | | 9 | | | 0.5 | 0.5 |
| Oil component according to the invention | 5 | 4 | 8 | 3 | 5 | 8 | 4 | 2 | 4 | 3 | 5 | 10 | 2 |
| Cetiol ® CC | 5 | 5 | 5 | | | | | 4 | | 5 | 3 | 4 | |
| Myritol ® 331 | 3 | 4 | | 4 | 4 | | | | 5 | | | 3 | 3 |
| Cetiol ® OE | | | | | 5 | | 3 | | 2 | | | | |
| Cetiol ® B | | | | 4 | | | | 4 | | 4 | | | |
| Cosmedia ® DC | 1 | 1 | 1 | 1 | 1 | 1.5 | 1.5 | 2 | 3 | 2 | 1.5 | 2 | 2 |
| Insect Repellent ® 3535 | | | | | | | 2 | | | | 5 | 5 | |
| Copherol ® F1300C | 1 | 1 | 1 | 1 | 1 | 1 | 1 | 1 | 1 | 1 | 1 | 1 | 1 |
| Zinc oxide NDM | 5 | 5 | 5 | 5 | 5 | | 2 | | 5 | 3 | | | |
| Eusolex ® T2000 | | | | 5 | 5 | | 2 | 3 | 5 | 2 | | | |
| Neo Heliopan ® AV | 7.5 | 7.5 | 7.5 | | | | 3 | 1 | 3 | 5 | | 5 | 5 |
| Parsol ® 1789 | | | | | | 2 | 2 | | | 1 | 2 | 2 | |
| Neo Heliopan ® MBC | | | | | | | 2 | | | | | | 2 |
| Uvinul ® T150 | | | | | | 1 | 1 | 2 | | | 1 | | |
| Uvasorb ® HEB | | | | | | 1 | 1 | 2 | | | 1 | 2 | |
| Neo Heliopan ® Hydro-Na salt, 15% aqueous solution | | | | | | | | | | | | | 13.3 |
| Glycerol | 3 | 3 | 3 | 3 | 3 | 3 | 3 | 3 | 3 | 3 | 3 | 5 | 5 |
| Veegum ® plus | 0.75 | 0.75 | | 0.5 | 0.5 | | 0.5 | | | 0.35 | | | |
| Keltrol T | 0.25 | 0.25 | | 0.5 | 0.5 | | 0.5 | | | 0.35 | | | |
| Cosmedia ® SP | | | 0.1 | | | 0.1 | 0.2 | | | | 0.1 | | |
| Permulen ® TR-2 polymer | | | | | | | | | 0.2 | 0.1 | | | |
| Water, perfume, preservative | q.s. | q.s. | q.s. | q.s. | q.s. | q.s. | q.s. | q.s. | q.s. | q.s. | q.s. | q.s. | q.s. |

TABLE 2

Formulations 14 to 26

| Components INCI (trade name) | 14 | 15 | 16 | 17 | 18 | 19 | 20 | 21 | 22 | 23 | 24 | 25 | 26 |
|---|---|---|---|---|---|---|---|---|---|---|---|---|---|
| Emulgade ® SE | 3.7 | 3.7 | | | | | | | | | | 4.9 | 4.1 |
| Eumulgin ® B1 | 1.3 | 1.3 | | | | | | | | | | | |
| Eumulgin ® B2 | | | | | | | | | | | | 1.1 | 0.9 |
| Emulgade ® PL 68/50 | | | 5 | 1 | 1 | 1 | 1 | 3 | | | | | |
| Eumulgin ® VL 75 | | | | | | | | | 3 | 5 | 5 | | |
| Lanette ® E | | | | 0.25 | 0.25 | 0.25 | 0.25 | .25 | | | | | |
| Amphisol K | | | 0.5 | | | | | | | | | | |
| Emulgade ® SUCRO | | | 0.5 | | | | | | | 0.5 | | 0.5 | 1 |

TABLE 2-continued

Formulations 14 to 26

| Components INCI (trade name) | 14 | 15 | 16 | 17 | 18 | 19 | 20 | 21 | 22 | 23 | 24 | 25 | 26 |
|---|---|---|---|---|---|---|---|---|---|---|---|---|---|
| Oil component according to the invention | 4 | 5 | 6 | 8 | 5 | 8 | 8 | 10 | 7 | 4 | 10 | 5 | 5 |
| Cetiol ® CC | 5 | | 5 | | | | | | 2.5 | 4 | 4 | 5 | 5 |
| Cetiol ® LC | | | | 1 | 1 | 1 | 1 | 1 | | | | | |
| Myritol ® 312 | | | | 1 | 1 | 1 | 1 | 1 | | | | | |
| Myritol ® 331 | | | | | | | | | | 4 | 4 | | |
| Cetiol ® SN | 3 | 3 | 3.5 | | | | | | | | | | |
| Eutanol ® G | | | | | | | | | 3.5 | 2 | 2 | | |
| Eutanol ® G16 | | | | 1 | 1 | 1 | 1 | 1 | | | | | |
| Cegesoft ® PS6 | | 1.5 | 1.5 | | | | | | | | | | |
| Cegesoft ® PFO | 1.5 | | | | | | | | | | | | |
| Silicone oil Wacker AK ® 350 | | | | 0.5 | 0.5 | 0.5 | 0.5 | 0.5 | | | | | |
| Cosmedia ® DC | 1 | | 1.5 | | | | | 1.5 | | 2.5 | 2.5 | | 0.5 |
| Hydagen ® C.A.T. | | | | | | | | | | | | 1.5 | |
| Copherol ® F 1300 C | | | | | | | | | 0.5 | 0.5 | 0.5 | | |
| Copherol ® 1250 C | 0.5 | 0.5 | | | | | | | | | | | |
| Ethanol | | | | | | | | | | | 5 | | |
| Locron ® L | | | | | | | | | | | | | 40 |
| Hydragen ® DCMF | | | | | | | | | | | | 0.1 | |
| Glycolic Acid | | | | | | | | | | | | 0.04 | |
| Glycerol | 2 | 2 | 2 | 3 | 3 | 3 | 3 | 3 | 2 | 2 | 2 | 3 | 2 |
| Potassium hydroxide, 20% aqueous solution | | | | | | 0.3 | 0.2 | 0.1 | 0.4 | 0.3 | 0.5 | | |
| Hispagel ® 50 | | | | | | | | | | 10 | | | |
| Carbomer | | | | | | | 0.1 | | 0.2 | | 0.2 | | |
| Cosmedia ® SP | | | | | 0.15 | | | | | | | | |
| Permulen ® TR-2 polymer | | | | | | 0.15 | | 0.05 | | | | | |
| Water, perfume, preservative | q.s. | q.s. | q.s. | q.s. | q.s. | q.s. | q.s. | q.s. | q.s. | q.s. | q.s. | q.s. | q.s. |

TABLE 3

Formulations 27 to 33 (formulations for antiperspirant/deodorant)

| Components INCI (trade name) | 27 | 28 | 29 | 30 | 31 | 32 | 33 |
|---|---|---|---|---|---|---|---|
| Emulgade ® SE-PF | 6 | | 4.5 | | | 6 | |
| Ceteareth-12 (Eumulgin ® B1) | | | | | | | |
| Ceteareth-20 (Eumulgin ® B2) | | | 1 | | | | |
| Emulgade ® CM | | | | 20 | | | |
| Lameform ® TGI | | 3 | | | | | |
| Novata ® AB | | | | | | | 4 |
| Lanette ® 18 | | | | 14.7 | | | |
| Cutina ® HR | | | | 3.7 | | | 6.5 |
| Dehymuls ® PGPH | | 1 | | | | | |
| Lanette ® E | 0.3 | | | | | 0.3 | |
| Lanette ® 22 | 2 | | | | 4 | | |
| Emulgade ® SUCRO | 0.8 | 1.3 | | 1 | | 2 | |
| Oil component according to the invention | 4 | 4 | 5 | 5 | 4 | 4 | 15 |
| Cetiol ® CC | | | 3 | | | | |
| Cetiol ® OE | 2 | | | 4 | | 3 | 9 |
| Myritol ® 331 | | | | | | | |
| Cetiol ® S | | | | 5 | 14.7 | | 20 |
| Dow Corning ® 246 Fluid | 3 | 5 | | 34 | | 2 | 14 |
| SFE ® 839 (GE Bayer) | | 3 | | | | | |
| Silicone oil Wacker AK ® 350 | 1 | | | | | | |
| Cosmedia ® DC | 1 | 1 | 1 | 1 | 1 | 1 | 1 |
| Hydagen ® C.A.T. | | | 2 | | | | |
| Eumulgin ® HRE 40 | | | | | 1 | | |
| Copherol ® 1250 C | | | | | 1 | | |

TABLE 3-continued

Formulations 27 to 33 (formulations for antiperspirant/deodorant)

| Components INCI (trade name) | 27 | 28 | 29 | 30 | 31 | 32 | 33 |
|---|---|---|---|---|---|---|---|
| Rezal ® 36 | 30 | 40 | | 22.9 | | 30 | 25 |
| Locron ® L | | | 10 | | | | |
| Hydragen ® DCMF | 0.05 | | | | | | |
| Glycolic Acid | 0.02 | | | | | | |
| Glycerol | | | 5 | 5 | | | |
| Propylene Carbonate | | | | | | | 0.5 |
| Bentone ® 18 | | | | | | | 1 |
| Talc | | | | | | 5 | 5 |
| MgSO4 × 7H2O | | | 1 | | | | |
| Water Phase II | 46.7 | | 35 | | | | |
| Water, perfume, preservative | q.s. | q.s. | q.s. | q.s. | q.s. | q.s. | q.s. |

27 - Antiperspirant/deodorant cream
28 - Antiperspirant cream (W/O)
29 - Antiperspirant/deodorant spray
30 - Antiperspirant stick with vitamin E
31 - Deodorant wipe - formulation
32 - Antiperspirant cream
33 - Antiperspirant cream "Soft Solid"

Table 4 describes sunscreen formulations of the O/W type; table 5 describes care emulsions. The use of the oil component according to the invention, in particular of preparation example A, positively influences the sensory behavior upon application. The quantitative data refer in each case to % by wt. of the standard commercial substances in the overall composition.

TABLE 4

O/W sunscreen emulsions

| Component | 1 | 2 | 3 | 4 | 5 | 6 | 7 | 8 | 9 | 10 | 11 |
|---|---|---|---|---|---|---|---|---|---|---|---|
| L = Lotion, C = Cream, S = Spray | L | C | L | C | L | C | S | C | C | L | L |
| Eumulgin ® VL 75 | 2 | | | | | 3 | | | 1 | | |
| Eumulgin ® B2 | | | | 2 | | | | | | 1 | |
| Tween ® 60 | | | | | | | | | | 1 | |
| Cutina ® E24 | | | | 0.5 | | | | | | | |
| Hostaphat ® KL 340 N | | | | | | | | | | | 0.5 |
| Eumulgin ® SG | | | 0.5 | | | 0.5 | | 0.3 | 0.1 | | |
| Lanette ® E | | | | | | | | 0.1 | 0.5 | | |
| Amphisol ® K | 0.5 | | | | | | 1 | | | | |
| Sodium stearate | | | | | 1 | | | | | | |
| Emulgade ® PL 68/50 | | 2 | 1 | | | 3 | | | | | |
| Emulgade ® SUCRO | | 2 | | | 1 | 1 | | | 3 | | 1 |
| Tego ® Care 450 | | 2 | | | | | | | 2 | | 1 |
| Cutina ® MD | | | | 2 | 1 | 3 | | | | | 1 |
| Lanette ® 14 | | 1 | | | | | | | | | |
| Lanette ® O | | | | 2 | | | | 2 | 1 | 1 | |
| Cutina ® PES | 1 | 1 | | 2 | | | | | | 1 | |
| Allianz ® OPT | 1 | | | 1 | 1 | | | 2 | | | 2 |
| Cosmedia ® DC | | 1.5 | 2 | | | 1.5 | 2 | | | 1.5 | 1.5 |
| Emery ® 1780 | | | | | 1 | 1 | | | | | |
| Lanolin, anhydrous, USP | | | | | | 1 | 1 | | | | |
| Oil component according to the invention | 6 | 2 | 4 | 7 | 3 | 7 | 6 | 6 | 4 | 4 | 5 |
| Myritol ® PC | | | | | | | | | 5 | | |
| Myritol ® 331 | 6 | | 4 | | | 5 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | | 2 | | | | | | 2 |
| Dow Corning DC ® 244 | | 2 | | | 1 | | | | | | |
| Dow Corning DC ® 2502 | | 1 | | | 1 | | | 3 | | | |
| Ceraphyl ® 45 | | | | | | | | | | 2 | 2 |
| Silicone oil Wacker AK ® 350 | | | | | 1 | | | | | | |
| Cetiol ® 868 | | 2 | | | | | | | | | |
| Cetiol ® J 600 | | 2 | | | | | | | | | |
| Mineral oil | | | | | 5 | | | | | | |
| Cetiol ® B | 4 | | 4 | | | | | 4 | | | |
| Eutanol ® G | | 3 | | | | 3 | | | | | |
| Eutanol ® G 16 S | 3 | | | | | | | | | | |
| Cetiol ® PGL | | | | | | | | | | 2 | |
| Photonyl ® LS | | | | | | | | | | | 2 |
| Panthenol | | | | | | | 1 | | | | |
| Bisabolol | | | | | | | 0.2 | | | | |
| Tocopherol/Tocopheryl | | | | | | | 1 | | | | |

TABLE 4-continued

| Component | \multicolumn{11}{c}{O/W sunscreen emulsions} |
|---|---|---|---|---|---|---|---|---|---|---|---|
|  | 1 | 2 | 3 | 4 | 5 | 6 | 7 | 8 | 9 | 10 | 11 |
| acetate |  |  |  |  |  |  |  |  |  |  |  |
| Neo Heliopan ® Hydro (Na salt) |  |  |  |  |  |  |  |  |  | 3 |  |
| Eusolex ® OCR | 6 |  | 9 |  | 5 | 7 | 9 |  | 4 |  | 7 |
| Neo Heliopan ® AP (Na salts) |  |  |  | 0.5 | 1 |  |  |  |  |  |  |
| Neo Heliopan ® BB |  |  |  |  |  |  |  | 1 | 1 |  | 1 |
| Neo Heliopan ® MBC |  | 2 |  | 1 |  |  |  | 3 | 1 |  | 3 |
| Neo Heliopan ® OS | 2 |  |  |  |  |  |  |  | 7 |  |  |
| Neo Heliopan ® E1000 |  | 4 |  |  |  |  |  | 5 |  |  |  |
| Neo Heliopan ® AV |  | 4 | 7.5 | 5 |  |  |  | 5 | 4 | 7.5 |  |
| Uvinul ® A PLUS |  |  |  |  | 1 |  | 2 |  |  |  |  |
| Uvinul ® T 150 | 1 |  |  |  |  |  |  |  | 1.3 | 1 | 1 |
| Tinosorb ® M |  | 2 |  |  | 2 |  | 2 |  |  |  |  |
| Tinosorb ® S |  | 1 |  |  | 2 |  | 2 |  |  |  |  |
| Parsol ® 1789 | 1 |  |  |  |  | 7 | 5 |  | 2 |  | 1 |
| Z-Cote ® HP 1 | 7 | 2 | 5 |  |  | 7 | 5 |  | 6 | 2 |  |
| Eusolex ® T 2000 | 5 | 2 |  | 10 |  |  | 10 |  |  | 2 |  |
| Veegum ® Ultra | 1.5 |  | 1.5 |  |  | 1.5 | 1.2 |  | 1 |  |  |
| Keltrol ® T | 0.5 |  | 0.5 |  |  | 0.5 | 0.4 |  | 0.5 |  |  |
| Cosmedia ® SP |  |  | 0.2 | 0.3 |  |  | 0.1 |  |  | 0.2 |  |
| Pemulen ® TR2 |  | 0.3 |  | 0.3 |  |  |  | 0.2 |  |  | 0.3 |
| Ethanol |  | 5 |  | 8 |  |  |  |  |  |  |  |
| Butylene glycol | 1 |  |  | 3 | 3 |  |  |  |  | 8 | 1 |
| Glycerol | 2 | 4 | 3 | 3 |  | 3 | 3 | 3 | 5 |  | 3 |
| Water/preservative/NaOH | \multicolumn{11}{c}{ad 100/q.s./q.s.} |

TABLE 5

| Component | \multicolumn{11}{c}{O/W care emulsions} |
|---|---|---|---|---|---|---|---|---|---|---|---|
|  | 12 | 13 | 14 | 15 | 16 | 17 | 18 | 19 | 20 | 21 | 22 |
| L = Lotion, C = Cream | C | C | L | C | L | C | L | L | L | L | C |
| Eumulgin ® VL 75 |  |  | 5 |  | 4 |  |  |  |  |  | 2 |
| Generol ® R |  |  |  |  |  | 2 |  |  |  |  |  |
| Eumulgin ® B2 |  |  |  |  |  |  |  |  |  | 1 |  |
| Tween ® 60 |  |  |  |  |  |  |  |  |  | 1 |  |
| Cutina ® E 24 |  |  |  | 0.5 |  |  |  |  |  |  |  |
| Eumulgin ® SG |  |  | 0.1 | 0.5 |  | 0.4 |  | 0.2 | 0.1 |  |  |
| Lanette ® E | 0.5 |  |  |  |  |  |  |  |  |  |  |
| Amphisol ® K | 0.5 | 0.5 |  |  |  |  |  |  |  |  |  |
| Sodium stearate |  |  |  |  | 1 |  |  |  |  |  |  |
| Emulgade ® PL 68/50 |  | 2 |  | 2 |  |  |  | 3 | 4 |  |  |
| Emulgade ® SUCRO | 2 | 1 | 1 | 1 |  |  |  |  |  |  | 2 |
| Tego ® Care 450 |  | 1 |  |  |  |  |  |  | 1 |  |  |
| Cutina ® MD | 2 | 1 | 1 | 1 |  | 5 |  |  |  | 2 |  |
| Lanette ® 14 |  |  |  |  | 1 |  |  | 2 |  | 1 |  |
| Lanette ® O | 2 |  |  | 2 | 1 | 3 | 1 |  | 1 | 1 | 3 |
| Cutina ® PES | 1 | 2 |  | 3 | 1 |  |  |  |  |  | 3 |
| Novata ® AB |  |  |  |  |  |  |  |  | 1 | 1 |  |
| Emery ® 1780 |  |  |  |  |  |  |  |  |  |  | 0.5 |
| Lanolin, anhydrous, USP |  |  |  |  |  | 4 |  |  |  |  |  |
| Cosmedia ® DC |  |  | 2 |  |  | 1.5 |  |  | 1 | 1 |  |
| Cetiol ® SB45 |  |  |  |  |  |  | 2 |  |  |  |  |
| Cegesoft ® C 17 | 2 |  |  |  |  |  |  |  |  |  |  |
| Oil component according to the invention | 5 | 5 | 4 | 4 | 3 | 4 | 5 | 4 | 5 | 10 | 2 |
| Myritol ® PC | 6 |  |  |  |  | 5 |  |  |  |  |  |
| Myritol ® 331 | 2 |  | 5 |  |  |  | 2 |  |  |  | 3 |
| Finsolv ® TN |  |  |  | 3 | 5 |  |  | 3 | 3 |  | 1 |
| Cetiol ® CC |  |  |  | 3 |  |  | 4 | 3 |  |  |  |
| Cetiol ® OE |  |  |  |  | 2 |  | 2 |  | 5 |  |  |
| Dow Corning DC ® 245 |  | 2 |  |  | 1 | 4 |  |  |  | 8 | 2 |
| Dow Corning DC ® 2502 |  | 1 |  |  | 1 |  |  |  |  |  | 3 |
| Prisorine ® 3758 | 3 |  |  |  |  |  |  |  |  |  | 2 |
| Silicone oil Wacker AK ® 350 |  |  |  |  | 1 |  |  |  |  |  | 1 |
| Cetiol ® 868 |  | 2 |  |  |  |  |  |  |  |  |  |
| Cetiol ® J 600 |  | 2 |  | 2 |  |  |  |  |  |  |  |

TABLE 5-continued

| | O/W care emulsions | | | | | | | | | | |
|---|---|---|---|---|---|---|---|---|---|---|---|
| Component | 12 | 13 | 14 | 15 | 16 | 17 | 18 | 19 | 20 | 21 | 22 |
| Ceraphyl ® 45 | | | | | | 3 | | | | | |
| Cetiol ® SN | | | 5 | | | | | | | | |
| Cetiol ® B | | 5 | | | | 5 | 4 | | | | 3 |
| Eutanol ® G | | 3 | 5 | | 5 | | | | | | |
| Cetiol ® PGL | | | | | | | | 5 | 2 | | |
| Dry Flo ® Plus | | 1 | | | | | | | | | 1 |
| SFE 839 | 1 | 1 | | | | | | | | | |
| Almond oil | | | | | | 2 | | | | | |
| Photonyl ® LS | | | | | | 2 | | | | | |
| Panthenol | | | | | | | 1 | | | | |
| Bisabolol | | | | | | | 0.2 | | | | |
| Tocopherol/Tocopheryl acetate | | | | | | | 1 | | | | |
| Veegum ® Ultra | | | | | | | | | 1 | | |
| Keltrol ® T | | | | | | | | | 0.5 | | |
| Cosmedia ® SP | 0.5 | | | | | 0.5 | 0.5 | 0.2 | | | 0.5 |
| Carbopol ® ETD 2001 | | 0.3 | | 0.3 | | | | | | | |
| Pemulen ® TR2 | | | 0.3 | | | 0.3 | | | | | |
| Ethanol | | 5 | | 8 | | | | | | | 10 |
| Butylene glycol | 5 | | 2 | 3 | 3 | | | | | 8 | |
| Glycerol | 2 | 4 | 3 | 3 | | 7 | 5 | 3 | 5 | | |
| Water, preservative, NaOH | | | | | | ad 100, q.s. (pH 6.5-7.5) | | | | | |

Formulations for Sun Protection and Skincare of the Water in Oil Type

Table 6 describes sunscreen formulations of the W/O emulsion type; table 7 describes care emulsions. The use of the oil component according to the invention, in particular of preparation example A, positively influences the sensory behavior upon application. The quantitative data refer in each case to % by wt. of the standard commercial substances in the overall composition.

TABLE 6

| | W/O sunscreen formulations | | | | | | | | | | |
|---|---|---|---|---|---|---|---|---|---|---|---|
| Component | 23 | 24 | 25 | 26 | 27 | 28 | 29 | 30 | 31 | 32 | 33 |
| L = Lotion, C = Cream | C | L | C | L | C | L | L | L | L | C | C |
| Dehymuls ® PGPH | 4 | 2 | 1 | 3 | 3 | 1 | 1 | 2 | 2 | 4 | 1 |
| Monomuls ® 90-O18 | | | 2 | | | | | | | | |
| Lameform ® TGI | 2 | | 4 | | 3 | | 4 | | | 1 | 3 |
| Abil ® EM 90 | | | | | | 4 | | | | | |
| Isolan ® PDI | | | | | | 4 | | 2 | | | |
| Zinc stearate | 1 | | | 1 | 1 | | | 1 | | 1 | |
| Beeswax | 1 | | 5 | 1 | | | | 5 | | 7 | 5 |
| Tego ® Care CG | | | | | 1 | | | | | | 0.5 |
| Emulgade ® SUCRO | 1 | 1 | | | 1 | | | 1 | | 1 | |
| Prisorine ® 3505 | | | 1 | | | 1 | 1 | | | | 1 |
| Cosmedia DC | 3 | 4 | 2 | 1 | 1 | 2 | 2 | 2 | 3 | 1 | 1 |
| Oil component according to the invention | 5 | 4 | 4 | 3 | 2 | 4 | 3 | 4 | 2 | 3 | 5 |
| Myritol ® 331 | 2 | | | 3 | 6 | | | | | | 3 |
| Finsolv ® TN | | | 5 | | | 2 | | | | | |
| Cetiol ® CC | 5 | | 2 | | 4 | 2 | | | 2 | 3 | 5 |
| Tegosoft DEC | | 4 | | 3 | | | 5 | 5 | | | |
| Cetiol ® OE | | | | | 4 | | 5 | | 4 | 2 | |
| Dow Corning ® DC 244 | | 3 | | | | | 2 | | 2 | 4 | |
| Dow Corning ® DC 2502 | 1 | | 1 | | 2 | 1 | | | | | 1 |
| Silicone oil Wacker AK 350 | | 1 | | 4 | | | | 3 | | | |
| Cetiol ® PGL | | 3 | | | | 2 | | | 4 | | |
| Cophero ® F 1300 | | | | | | | 1 | | | | |
| Magnesium sulfate x 7H$_2$O | | | | | | | 1 | | | | |
| Neo Heliopan ® Hydro (Na salt) | 2 | 2.2 | | 3 | 3 | | | | 1 | | 2 |
| Neo Heliopan ® 303 | | 5 | | | | | | | 4 | | 4 |
| Neo Heliopan ® BB | 2 | | | | | | 1 | 1 | | | |
| Uvasorb ® HEB | 1 | | 1 | 1 | | | | | | | 2 |
| Neo Heliopan ® MBC | 2 | | | | | 2 | 2 | 2 | | | |
| Uvinul ® A plus | | | | | | 2 | | | | 3 | 3 |

TABLE 6-continued

W/O sunscreen formulations

| Component | 23 | 24 | 25 | 26 | 27 | 28 | 29 | 30 | 31 | 32 | 33 |
|---|---|---|---|---|---|---|---|---|---|---|---|
| Neo Heliopan ® AP (Na salt) | | 2 | 2 | | 1 | | | | 1 | | 6 |
| Neo Heliopan ® AV | 3 | | 4 | 6 | 4 | 7.5 | 4 | 5 | | | 1 |
| Uvinul ® T 150 | 1 | 1 | | | 2.5 | | | 1 | | | |
| Parsol ® 1789 | 2 | 1 | | | | | 2 | | | 2 | 2 |
| Zinc oxide NDM | | | | | | 10 | | 3 | | | 4 |
| Tinosorb ® M | | 3 | | 3 | | | | 2 | | 2 | |
| Tinosorb ® S | | 3 | | 3 | | | | 2 | | 2 | |
| Eusolex ® T Aqua | | | 8 | | | | | 5 | | | |
| Eusolex ® T 2000 | | | | | 5 | | 3 | 3 | | | 4 |
| Ethanol | | | | | | | | | | 8 | |
| Glycerol | 5 | 3 | 3 | 3 | 5 | 3 | 2 | 3 | 10 | 4 | 3 |
| Water, preservative | | | | | ad 100, q.s. | | | | | | |

TABLE 7

W/O care emulsions

| Component | 34 | 35 | 36 | 37 | 38 | 39 | 40 | 41 | 42 | 43 | 44 |
|---|---|---|---|---|---|---|---|---|---|---|---|
| L = Lotion, C = Cream | C | L | C | L | C | L | L | L | C | C | C |
| Dehymuls ® PGPH | 1 | 3 | 1 | 2 | 3 | 1 | 1 | 2 | 1 | 1 | 1 |
| Monomuls ® 90-O18 | 2 | | | | | | | | 2 | | 2 |
| Lameform ® TGI | 4 | 1 | | | 3 | | | 1 | 4 | 3 | 3 |
| Abil ® EM 90 | | | | | | | 4 | | | | |
| Isolan ® PDI | | | | | | 4 | | | | | |
| Glucate ® DO | | | | 5 | | | | | | | |
| Ariacel ® 83 | | | 5 | | | | | | | | |
| Dehymuls ® FCE | | | | | | | | | | | |
| Dehymuls ® HRE 7 | | | | | | | | 4 | | 1 | |
| Zinc stearate | 2 | 1 | | 1 | 1 | | | 1 | 1 | 1 | |
| Microcrystalline wax | | | 5 | | | 2 | | | | | 5 |
| Beeswax | 4 | | | 1 | | | | 1 | 4 | 7 | |
| Emulgade ® SUCRO | 2 | 0.5 | | 1 | 1 | | 1 | | | | 1 |
| Tego Care ® CG | | | | | 1 | | | | | | 0.5 |
| Prisorine ® 3505 | | | 1 | 1 | | 1 | 1 | | | | 1 |
| Dry Flo ® Plus | | | | | | | | | | | |
| SFE 839 | | | | | | | 3 | | | | |
| Emery ® 1780 | 1 | | | | | | | | | | 1 |
| Lanolin; anhydrous USP | | | 5 | | | | | | | 4 | |
| Oil component according to the invention | 3 | 4 | 2 | 12 | 10 | 2 | 2 | 6 | 3 | 12 | 1 |
| Cegesoft ® C 17 | | | 3 | | | | | | | 1 | |
| Myritol ® PC | | | | | | 2 | | 4 | | | |
| Myritol ® 331 | 6 | | | | 2 | 6 | 2 | | | | 8 |
| Finsolv ® TN | | | | 5 | | 2 | 5 | | | | |
| Cetiol ® A | | 6 | | | | 4 | | | | | |
| Cetiol ® CC | | 8 | | | 2 | 2 | 2 | | | | 5 |
| Cetiol ® SN | | 5 | | | | | | 3 | | | |
| Cetiol ® OE | 3 | | | | 4 | | 2 | | 4 | 2 | |
| Dow Corning DC ® 244 | | | | | 1 | | 2 | | | | |
| Dow Corning DC ® 2502 | | | 1 | | 2 | | | | | | |
| Prisorine ® 3758 | | | | | 3 | | | | | | |
| Silicone oil Wacker AK ® 350 | | | | 4 | | | | 3 | | | |
| Cetiol ® 868 | | | | | | | | | | 2 | 7 |
| Cetiol ® J 600 | | | 4 | | | 2 | | | 2 | 6 | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G 16 | | 1 | | | | | | | | 3 | |
| Eutanol ® G | | | 3 | | | | | 8 | | | |
| Cetiol ® PGL | | | | | | 4 | | | 9 | | |
| Almond oil | | | | | 1 | | 5 | | | | |
| Insect Repellent ® 3535 | 2 | | | | | | | | | | |
| N,N-diethyl-m-toluamide | | | | | 3 | | 5 | | | | |
| Photonyl ® LS | 2 | 2 | | | | | | | | | |
| Panthenol | | | | | | 1.0 | | | | | |
| Bisabolol | | | | | | 0.2 | | | | | |

TABLE 7-continued

| W/O care emulsions | | | | | | | | | | | |
|---|---|---|---|---|---|---|---|---|---|---|---|
| Component | 34 | 35 | 36 | 37 | 38 | 39 | 40 | 41 | 42 | 43 | 44 |
| Tocopherol/Tocopheryl acetate | | | | | | 1.0 | | | | | |
| Magnesium sulfate × 7 water | | | | | | 1 | | | | | |
| Bentone ® 38 | | | | | 1 | | | | | | |
| Propylene carbonate | | | | | 0.5 | | | | | | |
| Ethanol | | | | | | | | | | 8 | |
| Butylene glycol | | | 2 | 6 | | | | 2 | 5 | | 2 |
| Glycerol | 5 | 3 | 3 | | 5 | 3 | 2 | | 10 | 4 | |
| Water, preservative | | | | | ad 100, q.s. | | | | | | |

APPENDIX

1) Abil ® EM 90
   INCI: Cetyl Dimethicone Copolyol
   Manufacturer: Tego Cosmetics (Goldschmidt)
2) Allianz ® OPT
   INCI: Acrylates/C12-22 Alkyl Methacrylate Copolymer
   Manufacturer: Rohm and Haas
3) Amphisol ® K
   INCI: Potassium Cetyl Phosphate
   Manufacturer: Hoffmann La Roche
4) Antaron ® V 220
   INCI: PVP/Eicosene Copolymer
   Manufacturer: GAF General Aniline Film Corp. (IPS-Global)
5) Antaron ® V 216
   INCI: PVP/Hexadecene Copolymer
   Manufacturer: GAF General Aniline Firm Corp. (IPS-Global)
6) Arlacel ® 83
   INCI: Sorbitan Sesquioleate
   Manufacturer: Uniqema (ICI Surfactants)
7) Arlacel ® P 135
   INCI: PEG-30 Dipolyhydroxystearate
   Manufacturer: Uniqema (ICI Surfactants)
8) Bentone ® 38
   INCI: Quaternium-18 Hectorite
   Manufacturer: Rheox (Elementis Specialties)
9) Carbopol ® 980
   INCI: Carbomer
   Manufacturer: Goodrich
10) Carbopol ® 2984
    INCI: Carbomer
    Manufacturer: Noveon, Inc.
11) Carbopol ® ETD 2001
    INCI: Carbomer
    Manufacturer: Noveon, Inc.
12) Carbopol ® Ultrez 10
    INCI: Carbomer
    Manufacturer: Noveon, Inc.
13) Cegesoft ® C 17
    INCI: Myristyl Lactate
    Manufacturer: Cognis Deutschland GmbH, Grünau
14) Cegesoft ® PFO
    INCI: Passiflora Incarnata (EU)
    Manufacturer: Cognis Deutschland GmbH
15) Cegesoft ® PS 6
    INCI: Olus
    Manufacturer: Cognis Deutschland GmbH
16) Ceraphyl ® 45
    INCI: Diethylhexyl Malate
    Manufacturer: International Specialty Products
17) Cetiol ® 868
    INCI: Ethylhexyl Stearate
    Manufacturer: Cognis Deutschland GmbH
18) Cetiol ® A
    INCI: Hexyl Laurate
    Manufacturer: Cognis Deutschland GmbH
19) Cetiol ® 8
    INCI: Dibutyl Adipate
    Manufacturer: Cognis Deutschland GmbH
20) Cetiol ® CC
    INCI: Dicaprylyl Carbonate
    Manufacturer: Cognis Deutschland GmbH
21) Cetiol ® J 600
    INCI: Oleyl Erucate
    Manufacturer: Cognis Deutschland GmbH
22) Cetiol ® LC
    INCI: Coco-Caprylate/Caprate
    Manufacturer: Cognis Deutschland GmbH
23) Cetiol ® OE
    INCI: Dicaprylyl Ether
    Manufacturer: Cognis Deutschland GmbH
24) Cetiol ® PGL
    INCI: Hexyldecanol, Hexyldecyl Laurate
    Manufacturer: Cognis Deutschland GmbH
25) Cetiol ® S
    INCI: Diethylhexylcyclohexane
    Manufacturer: Cognis Deutschland GmbH
26) Cetiol ® SB 45
    INCI: Shea Butter Butyrospermum Parkil (Linne)

APPENDIX-continued

27) Cetiol ® SN
    INCI: Cetearyl
    Isononanoate
    Manufacturer: Cognis
    Deutschland GmbH
28) Copherol ® F 1300 C
    INCI: Tocopherol
    Manufacturer: Cognis
    Deutschland GmbH
29) Copherol 1250 C
    INCI: Tocopheryl Acetate
    Manufacturer: Cognis
    Deutschland GmbH
30) Cosmedia ® DC
    INCI: Hydrogenated Dimer
    Dilinoleyl/Dimethylcarbonate
    Copolymer
    Manufacturer: Cognis
    Deutschland GmbH
31) Cosmedia ® SP
    INCI: Sodium Polyacrylate
    Manufacturer: Cognis
    Deutschland GmbH
32) Cutina ® E24
    INCI: PEG-20 Glyceryl
    Stearate
    Manufacturer: Cognis
    Deutschland GmbH
33) Cutina ® HR
    INCI: Hydrogenated Castor
    Oil
    Manufacturer: Cognis
    Deutschland GmbH
34) Cutina ® MD
    INCI: Glyceryl Stearate
    Manufacturer: Cognis
    Deutschland GmbH
35) Cutina ® PES
    INCI: Pentaerythrityl
    Distearate
    Manufacturer: Cognis
    Deutschland GmbH
36) Dehymuls ® FCE
    INCI: Dicocoyl
    Pentaerythrityl Distearyl
    Citrate
    Manufacturer: Cognis
    Deutschland GmbH
37) Dehymuls ® HRE 7
    INCI: PEG-7 Hydrogenated
    Castor Oil
    Manufacturer: Cognis
    Deutschland GmbH
38) Dehymuls ® PGPH
    INCI: Polyglyceryl-2-
    Dipolyhydroxystearate
    Manufacturer: Cognis
    Deutschland GmbH
39) Dow Corning ® 244 Fluid
    INCI: Cyclomethicone
    Manufacturer: Dow Corning
40) Dow Corning ® 246 Fluid
    INCI: Cyclopentasiloxane
    Manufacturer: Dow Corning
41) Dow Corning ® 2502
    INCI: Cetyl Dimethicone
    Manufacturer: Dow Corning
42) Dry ® Flo Plus
    INCI: Aluminum Starch
    Octenylsuccinate
    Manufacturer: National
    Starch
43) Elfacos ® ST 37
    INCI: PEG-22 Dodecyl
    Glycol Copolymer
    Manufacturer: Akzo-Nobel
44) Elfacos ® ST 9
    INCI: PEG-45 Dodecyl
    Glycol Copolymer
    Manufacturer: Akzo-Nobel
45) Emery ® 1780
    INCI: Lanolin Alcohol
    Manufacturer: Cognis
    Corporation (Emery)
46) Emulgade ® CM
    INCI: Cetearyl
    Isononanoate and
    Ceteareth-20 and Cetearyl
    Alcohol and Glyceryl
    Stearate and Glycerin and
    Ceteareth-12 and Cetyl
    Palmitate
    Manufacturer: Cognis
    Deutschland GmbH
47) Emulgade ® PL 68/50
    INCI: Cetearyl Glucoside,
    Cetearyl Alcohol
    Manufacturer: Cognis
    Deutschland GmbH
48) Emulgade ® SE-PF
    INCI: Glyceryl Stearate
    (and) Ceteareth-20 (and)
    Ceteareth-12 (and)
    Cetearyl Alcohol (and)
    Cetyl Palmitate
    Manufacturer: Cognis
    Deutschland GmbH
49) Emulgade ® SUCRO
    INCI: Sucrose
    Polystearate (and)
    Hydrogenated
    Polyisobutene
    Manufacturer: Cognis
    Deutschland GmbH
50) Emulgin ® B1
    INCI: Ceteareth-12
    Manufacturer: Cognis
    Deutschland GmbH
51) Eumulgin ® B 2
    INCI: Ceteareth-20
    Manufacturer: Cognis
    Deutschland GmbH
52) Eumulgin ® HRE 40
    INCI: PEG-40 Hydrogenated
    Castor Oil
    Manufacturer: Cognis
    Deutschland GmbH
53) Eumulgin ® SG
    INCI: Sodium Stearoyl
    Glutamate
    Manufacturer: Cognis
    Deutschland GmbH
54) Eumulgin ® VL 75
    INCI: Lauryl Glucoside
    (and) Polyglyceryl-2
    Dipolyhydroxystearate
    (and) Glycerin
    Manufacturer: Cognis
    Deutschland GmbH
55) Eusolex ® OCR
    INCI: Octocrylene
    Manufacturer: Merck
56) Eusolex ® T 2000
    INCI: Titanium Dioxide,
    Alumina, Simethicone
    Manufacturer: Merck
57) Eusolex ® T AQUA
    INCI: Water and Titanium
    Dioxide and Alumina and
    Sodium Metaphosphate and
    Phenoxyethanol and Sodium
    Methylparaben
    Manufacturer: Merck
58) Eutanol ® G
    INCI: Octyldodecanol
    Manufacturer: Cognis
    Deutschland GmbH APPENDIX-continued 59) Eutanol ® G 16
   INCI: Hexyldecanol
   Manufacturer: Cognis
   Deutschland GmbH
60) Eutanol ® G 16
   INCI: Hexyldecyl Stearate
   Manufacturer: Cognis
   Deutschland GmbH
61) Finsolv ® TN
   INCI: C 12/15 Alkyl
   Benzoate
   Manufacturer: Findex
   (Nordmann/Rassmann)
62) Generol ® R
   INCI: Brassica Campestris
   (Rapeseed) Sterols
   Manufacturer: Cognis
   Deutschland GmbH
63) Glucate ® DO
   INCI: Methyl Glucose
   Dioleate
   Manufacturer: NRC
   Nordmann/Rassmann
64) Hispagel ® 200
   INCI: Glycerin, Glyceryl
   Polyacrylate
   Manufacturer: Cognis
   Deutschland GmbH
65) Hostaphat ® KL 340 N
   INCI: Trilaureth-4
   Phosphate
   Manufacturer: Clariant
66) Hydagen ® C.A.T.
   INCI: Triethyl Citrate
   Manufacturer: Cognis
   Deutschland GmbH
67) Hydagen ® DCMF
   INCI: Chitosan
   Manufacturer: Cognis
   Deutschland GmbH
68) Insect Repellent ® 3535
   INCI: Ethyl Butylacetyl-
   aminopropionate
   Manufacturer: EMD
   Chemicals Inc.
69) Isolan ® PDI
   INCI: Diisostearoyl
   Polyglyceryl-3
   Diisostearate
   Manufacturer: Goldschmidt
   AG
70) Keltrol ® T
   INCI: Xanthan Gum
   Manufacturer: CP Kelco
71) Lameform ® TGI
   INCI: Polyglyceryl-3
   Diisostearate
   Manufacturer: Cognis
   Deutschland GmbH
72) Lanette ® 14
   INCI: Myristyl Alcohol
   Manufacturer: Cognis
   Deutschland GmbH
73) Lanette 18
   INCI: Stearyl Alcohol
   Manufacturer: Cognis
   Deutschland GmbH
74) Lanette ® 22
   INCI: Behenyl Alcohol
   Manufacturer: Cognis
   Deutschland GmbH
75) Lanette ® E
   INCI: Sodium Cetearyl
   Sulfate
   Manufacturer: Cognis
   Deutschland GmbH
76) Lanette ® O
   INCI: Cetearyl Alcohol
   Manufacturer: Cognis
   Deutschland GmbH 77) Locron ® L
   INCI: Aluminum
   Chlorohydrate
   Manufacturer: Clariant
78) Lucentite ® SAN
   INCI: Quaternium-18
   Hectorite
   Manufacturer: Co-Op
   Chemical Co. Ltd
79) Monomuls ® 90-O 18
   INCI: Glyceryl Oleate
   Manufacturer: Cognis
   Deutschland GmbH
80) Myrj ® 51
   INCI: PEG-30-Stearate
   Manufacturer: Uniqema
81) Myritol ® 312
   INCI: Caprylic/Capric
   Triglyceride
   Manufacturer: Cognis
   Deutschland GmbH
82) Myritol ® 331
   INCI: Cocoglycerides
   Manufacturer: Cognis
   Deutschland GmbH
83) Myritol ® PC
   INCI: Propylene glycol
   Dicaprylate/Dicaprate
   Manufacturer: Cognis
   Deutschland GmbH
84) Neo Heliopan ® 303
   INCI: Octocrylene
   Manufacture: Symrise
85) Neo Heliopan ® AP
   INCI: Disodium Phenyl
   Dibenzimidazole
   Tetrasulfonate
   Manufacturer: Symrise
86) Neo Heliopa ® AV
   INCI: Ethylhexyl
   Methoxycinnamate
   Manufacturer: Symrise
87) Neo Heliopan ® BB
   INCI: Benzophenone-3
   Manufacturer: Symrise
88) Neo Heliopan ® E 1000
   INCI: Isoamyl-p-
   Methoxycinnamate
   Manufacturer: Symrise
81) Neo Heliopan ® Hydro
   INCI: Phenylbenzimidazole
   Sulfonic Acid
   Manufacturer: Symrise
82) Neo Heliopan ® MBC
   INCI: 4-Methylbenzylidene
   Camphor
   Manufacturer: Symrise
83) Neo Heliopan ® OS
   INCI: Ethylhexyl
   Salicylate
   Manufacturer: Symrise
84) Novata ® AB
   INCI: Cocoglycerides
   Manufacturer: Cognis
   Deutschland GmbH
85) Parsol ® 1789
   INCI: Butyl
   Methoxydibenzoylmethane
   Manufacturer: Hoffmann-La
   Roche (Givaudan)
86) Pemulen ® TR-2 Polymer
   INCI: Acrylates/C10-30
   Alkylacrylate Cross-
   polymer
   Manufacturer: Noveon,
   Inc.
87) Photonyl ® LS
   INCI: Arginine, Disodium
   Adenosine Triphosphate,
   Mannitol, Pyridoxine HCL, APPENDIX-continued Phenylalanine, Tyrosine
    Manufacturer:
    Laboratoires
    Serobiologiques (Cognis)
88) Prisorine ® 3505
    INCI: Isostearic Acid
    Manufacturer: Uniqema
89) Prisorine ® 3758
    INCI: Hydrogenated
    Polyisobutene
    Manufacturer: Uniqema
90) Rezal 36G
    INCI: Aluminum Zirconium
    Tetrachlorohydrex GLY
    Manufacturer: Reheis,
    Inc.
91) SFE ® 839
    INCI: Cyclopentasiloxane
    and Dimethicone/Vinyl
    Dimethicone Crosspolymer
    Manufacturer: GE
    Silicones
92) Silicone Oil Wacker AK ®
    350
    INCI: Dimethicone
    Manufacturer: Wacker
93) Tego ® Care 450
    INCI: Polyglyceryl-3
    Methylglucose Distearate
    Manufacturer: Tego
    Cosmetics (Goldschmidt)
94) Tego ® Care CG 90
    INCI: Cetearyl Glucoside
    Manufacturer: Goldschmidt
95) Tegosoft ® DEC
    INCI: Diethylhexyl
    Carbonate
    Manufacturer: Goldschmidt
96) Tinosorb ® S
    INCI: Bis-
    Ethylhexyloxyphenol
    Methoxyphenyl Triazine
    Manufacturer: Ciba
    Specialty Chemicals
    Corporation
97) Tinosorb ® M
    INCI: Methylene Bis-
    Benzotriazolyl
    Tetramethylbutylphenol
    Manufacturer: Ciba
    Specialty Chemicals
    Corporation
98) Tween ® 60
    INCI: Polysorbate 60
    Manufacturer: Uniqema
    (ICI Surfactants)
99) Uvasorb ® HEB
    INCI: Diethylhexyl
    Butamido Triazone
    Manufacturer: 3V Inc.
100) Unirep ® U-18
    INCI: Dimethyl Phthalate
    and Diethyl Toluamide and
    Ethyl Hexanediol
    Manufacturer: Induchem AG
101) Uvinul ® T 150
    INCI: Ethylhexyl Triazone
    Manufacturer: BASF
102) Uvinul ® A plus
    INCI: Diethylamino
    Hydroxybenzoyl Hexyl
    Benzoate
    Manufacturer: BASF
103) Veegum ® Ultra
    INCI: Magnesium Aluminium
    Silicate
    Manufacturer: R.T. Vanderbilt
    Company, Inc.
104) Veegum ® Plus
    INCI: Magnesium Aluminum
    Silicate and Cellulose
    Gum
    Manufacturer: R.T. Vanderbilt
    Company, Inc.
105) Z-Cote ® HP 1
    INCI: Zinc Oxide and
    Triethyoxycaprylylsilane
    Manufacturer: BASF
106) Zinc Oxide NDM
    INCI: Zinc Oxide
    Manufacturer: Symrise

What is claimed is:

1. An alkyl benzoate-containing mixture, comprising:
(a) C12 alkyl benzoate(s), in an amount greater than or equal to 60% of the mixture, and
(b) C14 alkyl benzoate(s), in an amount from about 15% and to about 40%, said percentages being weight percent based on the total sum of the alkyl benzoates and wherein the sum of the branched alkyl benzoates is less than or equal to about 10% by weight, based on the total sum of the alkyl benzoates.

2. The alkyl benzoate-containing mixture of claim 1, wherein the sum of the alkyl benzoates with an alkyl carbon chain length of less than or equal to 10, is less than or equal to about 3% by weight, based on the total sum of the alkyl benzoates.

3. The alkyl benzoate-containing mixture of claim 1, wherein the sum of the alkyl benzoates with a carbon chain length of greater than 14 is less than or equal to about 15% by weight, based on the total sum of the alkyl benzoates.

4. A cosmetic and/or pharmaceutical preparation comprising at least one alkyl benzoate mixture of claim 1, and at least one UV photoprotective filter.

5. The alkyl benzoate-containing mixture of claim 1, wherein said percentage of alkyl benzoate(s) having an alkyl moiety containing an uneven number of carbon atoms, is less than or equal to about 30% by weight, based on the total sum of the alkyl benzoates.

6. The alkyl benzoate-containing mixture of claim 1, wherein said C12 alkyl benzoate(s) comprise greater than or equal to about 70% by weight, and said C14 alkyl benzoates comprise between about 25% and about 30% by weight, based on the total sum of the alkyl benzoates.

7. The alkyl benzoate-containing mixture of claim 2, wherein said sum of the alkyl benzoate(s) with an alkyl carbon chain length of less than or equal to 10, is less than or equal to about 1% by weight, based on the total sum of the alkyl benzoates.

8. The alkyl benzoate-containing mixture of claim 3, wherein said sum of the alkyl benzoate(s) with a carbon chain length of greater than 14 is less than or equal to about 4% by weight, based on the total sum of the alkyl benzoates.

9. The alkyl benzoate-containing mixture of claim 1, wherein said sum of the branched alkyl benzoate(s) is less than or equal to about 5% by weight, based on the total sum of the alkyl benzoates.

10. A method of preparing cosmetic and/or pharmaceutical preparations comprising incorporating the alkyl benzoates of claim 1 in cosmetic and/or pharmaceutical compositions.

11. The method of claim 10, wherein said alkyl benzoates are incorporated into said cosmetic and/or pharmaceutical compositions as oil components.

\* \* \* \* \*